United States Patent [19]

Quick

[11] 4,388,279
[45] Jun. 14, 1983

[54] RECOVERY OF METAL VALUES FROM ORGANIC REACTION PRODUCTS

[75] Inventor: Michael H. Quick, Palatine, Ill.

[73] Assignee: UOP Inc., Des Plaines, Ill.

[21] Appl. No.: 270,203

[22] Filed: Jun. 3, 1981

[51] Int. Cl.³ .............................................. C01G 55/00
[52] U.S. Cl. ................... 423/22; 75/101 BE; 252/411 R; 568/909
[58] Field of Search ...................... 423/22; 75/101 BE; 252/411 R

[56] References Cited

U.S. PATENT DOCUMENTS

| | | | |
|---|---|---|---|
| 3,892,689 | 2/1975 | Motani et al. | 423/22 |
| 3,922,231 | 11/1975 | Carlin et al. | 423/22 |
| 3,994,719 | 11/1976 | Corte et al. | 423/22 |
| 3,999,983 | 12/1976 | Grosbois et al. | 423/22 |
| 4,069,040 | 1/1978 | Thomas et al. | 423/22 |
| 4,130,625 | 12/1978 | Evers et al. | 423/22 |
| 4,203,952 | 5/1980 | Hancock et al. | 423/22 |
| 4,257,807 | 3/1981 | Drobot | 423/22 |
| 4,272,288 | 6/1981 | Dessan | 423/22 |
| 4,312,779 | 1/1982 | Quick | 423/22 |

Primary Examiner—Herbert T. Carter
Attorney, Agent, or Firm—James R. Hoatson, Jr.; Raymond H. Nelson; William H. Page, II

[57] ABSTRACT

Trace amounts of catalysts which are present in products resulting from organic reactions, such as rhodium which is present in the alcohol products resulting from a hydroformylation reaction, may be removed by treating the aforesaid products with a solid adsorbent such as a metal compound of Groups IA or IIA of the Periodic Table, molecular sieves or ion-exchange resins at a temperature in the range of from about ambient to about 100° C. and a pressure in the range of from about atmospheric to about 100 atmospheres.

2 Claims, No Drawings

RECOVERY OF METAL VALUES FROM ORGANIC REACTION PRODUCTS

BACKGROUND OF THE INVENTION

Many organic reactions involve the use of catalysts and particularly metal-containing catalysts. When utilizing these catalysts which may contain the metal in elemental form or as a metallic component, it becomes necessary to recover the catalyst or the metal contained therein in order to render the process economically viable. This is especially true when employing noble metals such as the noble metals of Group VIII of the Periodic Table including platinum, palladium, ruthenium, rhodium, osmium, iridium or other metals such as gold, silver, or rhenium. Due to the high cost of these metals, it is imperative that, as hereinbefore set forth, the loss of said metals be kept to a minimum in order to maintain the overall cost of the reaction at the lowest possible point. As an example of the type of organic reaction involving the use of a noble metal, a hydroformylation reaction may be cited. In this type of reaction, an olefinic hydrocarbon may be treated with carbon monoxide and hydrogen in the presence of a rhodium-containing compound which acts as the catalyst therefor in a one-step process to prepare an alcohol.

The commercialization of processes for the synthesis of alcohols utilizing a rhodium complex is affected by the difficulty which is attendant in the recovery of rhodium. A particular disadvantage which negates the commercial use of such complex catalysts comprises the frequent loss of the precious metal which may occur in process conditions. The loss of only a trace amount of this precious metal makes the process uneconomical to operate and overshadows the technological conversion rate and selectivity rate which is obtained when using this metal. The separation of the rhodium catalyst from alcohol products, especially high molecular weight alcohols, by conventional means such as distillation is not practical inasmuch as the unstable rhodium complex has a tendency to decompose in the distillation apparatus, thus resulting in the loss of rhodium by plating or precipitation on the surface of the process equipment.

The rhodium-containing catalyst may be recovered to a relatively great extent from the alcohol products of the hydroformylation reaction by treating the alcohol with various chemical compounds including ammonium hydroxide in either an aqueous or anhydrous state, with various nitrogen-containing compounds such as amines either primary, secondary or tertiary in nature, etc. In the event that an aqueous ammonium hydroxide solution is employed as a treating agent, the rhodium complex may be separated from the organic product phase and will be retained in the aqueous phase. The latter can then be recycled to the hydroformylation zone for use as a catalyst therein. However, the liquid product phase will still contain a trace amount of rhodium and therefore, it is necessary to recover or substantially decrease this trace amount of rhodium still present in said product. As will hereinafter be shown in greater detail, it has now been discovered that by contacting an organic reaction product with a solid adsorbent of the type hereinafter set forth in greater detail, it is possible to remove a relatively large amount of the trace metal present in said product and recover said metal for further use.

SUMMARY OF THE INVENTION

This invention relates to a process for the recovery of trace metals from products resulting from a reaction involving the use of said metals as a catalyst therefor. More particularly, the invention is concerned with a process for the recovery of trace amounts of noble metals which have been used as catalysts for organic reactions.

Various organic reactions involve the use of metal-containing catalysts. In many instances, these metallic catalysts contain noble metals which may, due to the particular nature of the catalyst, be retained in the product which is obtained from the particular reaction. One such type of reaction involves the formation of alcohols which are important basic chemicals utilized in a wide variety of facets in the chemical industry. For example, isopropyl alcohol is used in the manufacture of acetone which, in turn, is a source of acetic anhydride, diacetone alcohol, methyl isobutyl ketone, etc. or it may be used as a solvent in, for example, oils, gums, resins, etc; as an anti-stalling agent in liquid fuels, etc. Likewise, dodecyl alcohol, which is also known as lauryl alcohol, is used in the manufacture of synthetic detergents, lube additives, pharmaceuticals, rubber, textiles and perfumes, while tetradecanol, which is also known as myristyl alcohol, is used as a plasticizer, anti-foam agent, as a perfume fixitive, for soaps and cosmetics, etc.

It is therefore an object of this invention to provide a process for the recovery of metals.

A further object of this invention is found in a process for the recovery of trace amounts of metals which are present in products resulting from organic reactions in which the metal was used as a catalyst therefor.

In one aspect, an embodiment of this invention is found in a process for the recovery of trace amounts of metal from the products resulting from a reaction involving the use of said metal as a catalyst therefor which comprises contacting said products with a solid adsorbent selected from the group consisting of salts of metals from Group IA and Group IIA of the Periodic Table, molecular sieves and an ion exchange resin at process conditions, and recovering said metal.

A specific embodiment of this invention is found in a process for the recovery of trace amounts of rhodium from alcohols resulting from a hydroformylation reaction involving the use of said rhodium as a catalyst therefor which comprises contacting said alcohol with a solid adsorbent comprising calcium sulfate at a temperature in the range of from about ambient to about 100° C. and a pressure in the range of from about atmospheric to about 100 atmospheres, and recovering said rhodium.

Other objects and embodiments will be found in the following further detailed description of the invention.

DETAILED DESCRIPTION OF THE INVENTION

As hereinbefore set forth, the present invention is concerned with a process for the recovery of trace amounts of metals from products resulting from organic reactions in which the metals have been used as catalysts therefor. Particularly, the invention is concerned with a process for the recovery of trace amounts of noble metals which, due to the costly nature of said metals, make as complete a recovery as possible imperative in order to maintain the cost of the reactions involving the use of these metals as low as possible. The trace amounts of metals which remain in organic reaction products is effected by contacting the aforesaid products with a solid adsorbent of the type hereinafter set forth in greater detail at process conditions. The process conditions which are employed for the recovery of these trace amounts of metals will include a temperature in the range of from about ambient up to about 100° C. or more and a pressure which may range from atmospheric up to about 100 atmospheres or more. The contact of the reaction products with the solid adsorbent will take place for a period of time which may range from about 0.1 up to about 24 hours or more in duration. The particular operating parameters which are utilized in this invention will be dependent upon the various factors including the type of reaction product which contains the metal, the metal itself, as well as an interrelation between temperature and pressure.

The solid adsorbents which are utilized to recover the trace amounts of metals will include salts of the metals of Group IA and Group IIA of the Periodic Table, the preferred salts which are employed will include lithium carbonate, lithium sulfate, sodium carbonate, sodium sulfate, potassium carbonate, potassium sulfate, rubidium carbonate, rubidium sulfate, cesium carbonate, cesium sulfate, manganese carbonate, manganese sulfate, calcium carbonate, calcium sulfate, strontium carbonate, strontium sulfate, barium carbonate, barium sulfate, zeolitic compositions as exemplified by molecular sieves, the preferred type of molecular sieves being those which possess a relatively small pore size such as 13X molecular sieves in which the cation present may be sodium, potassium, lithium, etc; and ion-exchange resins, particularly anion-exchange resins such as those sold under the trade name of Amberlyst A-21, Amberlyst A-26, Amberlyst A-27, Amberlite IRA-47S, Amberlite IRA-400C, Amberlite IRA-402, etc. It is to be understood that the aforementioned list of solid adsorbents are only representative of the class of adsorbents which may be used, although not necessarily with equivalent results.

As an illustration of one type of organic reaction to which the process of the present invention is applicable, an olefinic hydrocarbon which is to be hydroformylated is charged to a pressure-resistant apparatus such as an autoclave of the rotating, mixing or stirring type which contains a rhodium complex catalyst and, if so desired, an amine compound which will act as a modifier therefor. The autoclave is sealed, following which carbon monoxide and hydrogen are pressured in until the desired operating pressure has been obtained. Thereafter, the reactor is heated to the desired operating temperature and maintained thereat for a predetermined period of time. Following the completion of the desired reaction period, heating is discontinued and after the apparatus has returned to room temperature, the excess pressure is discharged and the reaction mixture is recovered therefrom. The recovered reaction mixture which contains the reaction product comprising an alcohol in which the rhodium catalyst is dissolved is then placed in a second apparatus wherein the reaction mixture is contacted with what, for purposes of the present invention, will be designated as a stripping agent such as aqueous ammonium hydroxide, anhydrous ammonia, an amine compound, etc. Upon completion of the extraction or treatment period, the stripping agent solution containing substantially all of the rhodium complex catalyst is separated from the organic phase which comprises the alcohol product and the amine modifier. The product alcohol which still contains a trace amount of the rhodium complex catalyst is then treated in a manner hereinafter set forth in greater detail whereby substantially all of the trace amounts of the catalyst are recovered from the product alcohol which may then be separated from the amine modifier by conventional means and passed to storage.

The removal of trace amounts of metal from reaction products by contacting the reaction products with a solid adsorbent of the type hereinbefore set forth in greater detail may be effected in either a batch or continuous manner of operation. For example, when a batch type operation is employed, the reaction product is placed in an appropriate apparatus which may be exposed to the atmosphere, or, in the event that elevated temperatures and pressures are to be employed, a pressure resistant vessel such as an autoclave. The contact of the solid adsorbent with the reaction product takes place during storage for a predetermined period of time which, as previously discussed, will be dependent upon the operating parameters of temperature and pressure within the aforesaid ranges. Upon completion of the desired residence time, the mixture is recovered and the organic reaction product is separated from the adsorbent by conventional means such as filtration, decantation, centrifugation, etc.

The solid adsorbent which contains the metal may then be treated in any manner known in the art to recover the desired metal. For example, as an illustration of one type of recovery process, the salt of a metal of Group IIA of the Periodic Table, such as calcium sulfate which has been used to adsorb the metal, may then be subjected to an evaporation process which is effected at an elevated temperature and, if so desired, an elevated pressure to evaporate any excess reaction product which has been retained on the surface of the adsorbent. After removal of the reaction product, the salt is then subjected to a heat treatment which may be in the range of from about 100° to about 400° C. and in the added presence of a reducing agent such as hydrogen whereby the metal which may be in the form of a complex or salt is decomposed to the elements of valent state. Upon reaching this state, the salt which is soluble in water is leached with water to remove the soluble salt while retaining the elemental metal. The elemental metal then can be recovered by filtration, centrifugation, etc. for reuse as a catalyst, either in this state or after having been utilized as one component in the formation of a desired catalytic salt or complex.

It is also contemplated within the scope of this invention that the recovery of the metal from the organic reaction product may be effected in a continuous manner of operation. When such a type of operation is utilized, the organic reaction product containing the metal, after having undergone process steps similar in nature to those hereinbefore set forth wherein a major portion of the catalytic metal is recovered is continuously passed through a column of the solid adsorbent at a predetermined flow rate. This flow rate may be at a liquid hourly space velocity of from about 0.1 to about 3 hours$^{-1}$. The recovery of the trace amount of metals is preferably effected at ambient temperature and atmospheric pressure, although other operating parameters within the range hereinbefore set forth may also be employed. After utilizing this solid adsorbent bed for a predetermined period of time, the flow of organic product may be discontinued and the adsorbent bed then subjected to conventional means of metal recovery similar in nature to that previously described.

The following examples are given for purposes of illustrating the process of the present invention. However, it is to be understood that these examples are given merely for purposes of illustration and that the present process is not necessarily limited thereto.

EXAMPLE I

An organic reaction product was obtained by reacting 400 grams of a $C_{11}$ olefin, 70 grams of dimethyldodecylamine, and 0.38 grams of a catalyst comprising hexarhodium hexadecalcarbonyl in a rotating stainless steel autoclave. The autoclave was sealed and 200 atmospheres of a 1:1 blend of carbon monoxide and hydrogen was charged thereto at room temperature. The autoclave was then heated to a temperature of 150° C. and maintained thereat for a period of 6 hours. At the end of the 6 hour period, heating was discontinued and, after the autoclave was allowed to return to room temperature, the excess pressure was discharged and the reaction mixture was recovered therefrom.

The product which consisted of a mixture of dodecyl alcohols, dimethyldodecylamine and a soluble rhodium compound was then extracted four times at room temperature with an approximately equal amount of a concentrated aqueous ammonia solution (28%) to remove the rhodium. The organic phase was then washed twice with an approximate equal weight of water for a period of time ranging from about 5 minutes to about 10 minutes to remove any ammonia which was dissolved in the organic product. At this time period, the dodecyl alcohol/dimethyldodecylamine mixture contained 1.5 ppm of rhodium which could not be removed by further extraction.

The aforesaid raffinate (250 grams) was placed in a flask along with 70 grams of calcium sulfate and was stored at ambient temperature under a nitrogen blanket for a period of 24 hours, the flash being subjected to occasional agitation. At the end of the 24 hour period, the adsorbent and organic product were separated by filtration. Analysis of the organic product disclosed that the alcohol contained only 0.37 ppm of rhodium, thus indicating that approximately 75% of the rhodium had been removed from the alcohol.

EXAMPLE II

In this example, a raffinate comprising a mixture of dodecyl alcohol and dimethyldodecylamine (DMDA) was prepared in a manner similar to that set forth in Example I above. To illustrate the operability of a trace metal removal from a product in a continuous manner of operation, 230 grams of the raffinate which contained 0.9 ppm of rhodium was passed through a column of calcium sulfate. The calcium sulfate in an amount of 156 grams was contained in a glass column, the bed of adsorbent measuring 2.5×40 cm. The raffinate was passed through the column at a rate of about 2.5 ml per minute at ambient temperature and pressure under a nitrogen blanket. Analysis of the product which was recovered after passage through the calcium sulfate bed indicated that the rhodium content of the raffinate had been reduced to 0.26 ppm rhodium, thus indicating that there had been a 71% removal of the rhodium from the product.

EXAMPLE III

It is also contemplated that organic reaction products resulting from reactions involving the use of metal catalysts containing platinum and palladium and which contain trace amounts of these metals may be extracted with other solid adsorbents such as barium sulfate, potassium sulfate, potassium carbonate, sodium carbonate, Amberlyst A-27 at ambient temperature under a nitrogen blanket to remove and recover a substantial portion of the trace amounts of the aforesaid metals present in the products.

I claim as my invention:

1. A process for the recovery of rhodium metal complex catalyst from a liquid hydroformylation alcohol reaction product obtained from treatment of an olefinic hydrocarbon with hydrogen and carbon monoxide in the presence of said rhodium metal complex catalyst at hydroformylation conditions, which recovery process comprises treating said hydroformylation alcohol reaction product with an effective amount of ammonia to remove the bulk of the rhodium contained therein, separating the alcohol product solution containing residual amounts of rhodium, thereafter contacting said solution with solid calcium sulfate at adsorption conditions to separate such residual rhodium from the solution and recovering rhodium valves.

2. The process as set forth in claim 1 in which said adsorption conditions include a temperature in the range of from about ambient to about 100° C. and a pressure in the range of from about atmospheric to about 100 atmospheres.

* * * * *